United States Patent [19]

Craig et al.

[11] Patent Number: Plant 7,576

[45] Date of Patent: Jul. 2, 1991

[54] GERANIUM PLANT 'CENTENNIAL'

[75] Inventors: Richard Craig; Leon Glicenstein, both of State College, Pa.

[73] Assignee: Research Corporation Technologies, Inc., Tucson, Ariz.

[21] Appl. No.: 384,955

[22] Filed: Jul. 18, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Scully, Scott, Murphy & Presser

[57] ABSTRACT

This invention relates to a new and distinct cultivar of geranium (*Pelargonium*×*Xhortorum*) named 'Centennial' substantially as described herein, characterized as being particularly well adapted to both commercial greenhouse production and garden performance, and as being early flowering, floriferous, self-branching, compact and producing bright scarlet semidouble flowers.

1 Drawing Sheet

The present invention relates to a new and distinct cultivar of geranium (*Pelargonium*×*Xhortorum*) called 'Centennial'. This cultivar is early flowering, floriferous, self-branching, compact, and produces bright scarlet, semidouble flowers. Moreover, the cultivar is particularly well adapted to both commercial greenhouse production and garden performance.

The cultivar was developed from an organized, scientifically designed breeding program carried out at the Department of Horticulture, The Pennsylvania State University, University Park, Pa. 16802. The breeding program was designed to create new geranium genotypes with clear, bright colors which combined the flowering ability and compactness of European cultivars with the heat tolerance, low-light tolerance, and excellent greenhouse production qualities of Penn State material. The pedigree of this cultivar is as follows:

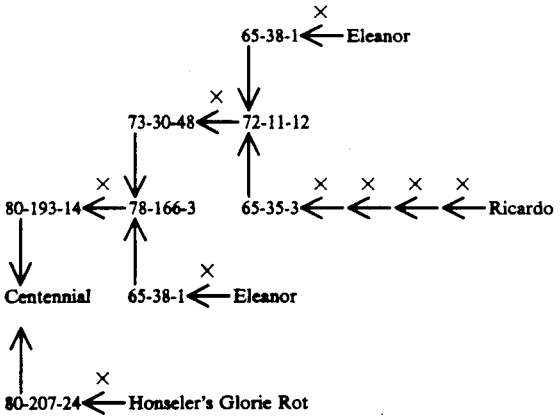

Centennial may share some common traits with the patented cultivar '#(812)-(82-116-13)' because they are selections from the same parentage and because they both conform to the general selection criteria designed into the breeding program. 'Centennial' is distinguished from '#821-(82-116-13)' by having: longer internodes and leaf petioles which result in a larger yet compact plant; a substantially greater number of florets per inflorescence which improves floral conformation; a greater floret which adds to the attractiveness of individual florets, number of petals per and by shorter peduncles which place the inflorescences closer to the foliage and provide a much more balanced floral display. In addition, floral pigmentation is more uniform; 'Centennial' does not exhibit the dark red spot which is characteristic of '#821-(82-116-13)'.

The selection was asexually propagated by cuttings and the reproductions ran true.

BRIEF DESCRIPTION OF THE DRAWING

The FIGURE illustrates in color the cultivar including foliage and flowers.

With reference to the detailed description of the cultivar which follows, the test plant was grown in a glasshouse under full, natural light, at a night temperature of approximately 58° F., and a day temperature of approximately 68° F. Soilless medium was fertilized with every watering with 200 ppm nitrogen from 15-16-17.

Color readings were taken under incandescent light at 200 foot candles and color identification was by reference to the Royal Horticultural Society Colour Charts, except where common terms of color definition are employed.

THE PLANT

Classification:

*Botanical.*—*Pelargonium*×*Xhortorum.*

*Tradename.*—'Centennial'.

Form: Compact, self-branching.

Height: 12.0–24.0 cm.

Growth: Free branching from base; Short internodes; Stands upright with no artificial support.

Leaves:

*Size.*—Largest leaf 5.5 cm long×10.0 cm wide; Ratio of length to width approximately 1:2.

*Shape.*—Reniform, variously lobed.

*Margin.*—Crenate.

*Texture.*—Pubescent; Dull.

*Color.*—Adaxial: Distal: Green 137A; Zone: Greyed-purple 187A overlaid with green 137A; Proximal: Green 137B. Abaxial: Green 137B.

*Ribs and veins.*—Palmate venation; Veins recessed and prominent.

*Petioles.*—Length: 6.6 to 9.7 cm. Color: Green 137B.

Stem:

*Internode length.*—1.5 to 1.9 cm.

*Color.*—Green 143C.

THE FLOWER

Blooming habit: Continuous.

Inflorescence:

*Form.*—Umbellate.

*Size.*—10 cm across when fully open.

Persistence: Persistent, non-shattering.

Disease resistance: Not known; favorable in outdoor trials.

Florets:

*Number.*—40 to 50 florets per inflorescence.

*Form.*—Flat to cupped.

*Size.*—2.0–4.0 cm across open floret.

Petals:

*Number.*—7–10.

*Texture and appearance.*—Smooth to slightly wrinkled.

*Color.*—Upper petals: Adaxial: Distal two-thirds: Red 44A; Proximal one-third: Red 40A with veins red 44A; Base: Small area of white 155D. Abaxial: Red 40A with base white 155D. Lower Petals: Adaxial: Red 44A with base white 155D. Abaxial: Distal two-thirds: Red 40A; Proximal one-third: Red 40B; Base: Small area of white 155D.

Petaloids:

*Number.*—0, 1, 2 or 3.

*Shape.*—Variable; often misshapen.

*Color.*—Similar to the color of the petals.

Sepals:

*Number.*—Usually 5.

Pedicel:

*Length.*—1.9–2.5 cm.

*Color.*—Green 146C proximal. Greyed-red 178 distal.

Peduncle: Arises from node; opposed to leaf petiole; thick (up to 5.0 mm in diameter).

*Length.*—12.0 to 13.8 cm.

*Color.*—Yellow-green 144A.

REPRODUCTIVE ORGANS

Androecium:

*Stamens.*—6–8 flat, ribbon-like filaments, joined at their bases; Versatile attachment to anthers which are light purple and well developed; 2 sizes of orange pollen.

*Staminodes.*—1–2 flat, ribbon-like filaments with no anthers.

*Petaloid stamens.*—1–2 petal-like filaments with partially developed anthers.

Gynoecium:

*Pistil number.*—1.

*Length.*—7.0–10.0 mm.

*Stigma.*—5-parted; Light purple.

*Style.*—1.0–2.5 mm long; Green.

*Ovary.*—4.0 mm long; Superior; Very pubescent.

Fruit: Achene schizocarp; Rarely observed.

What is claimed is:

1. A new and distinct cultivar of geranium substantially as shown and described herein, characterized as being particularly well adapted to both commercial greenhouse production and garden performance and as being early flowering, floriferous, self-branching, compact, and producing bright scarlet, semidouble flowers.

* * * * *

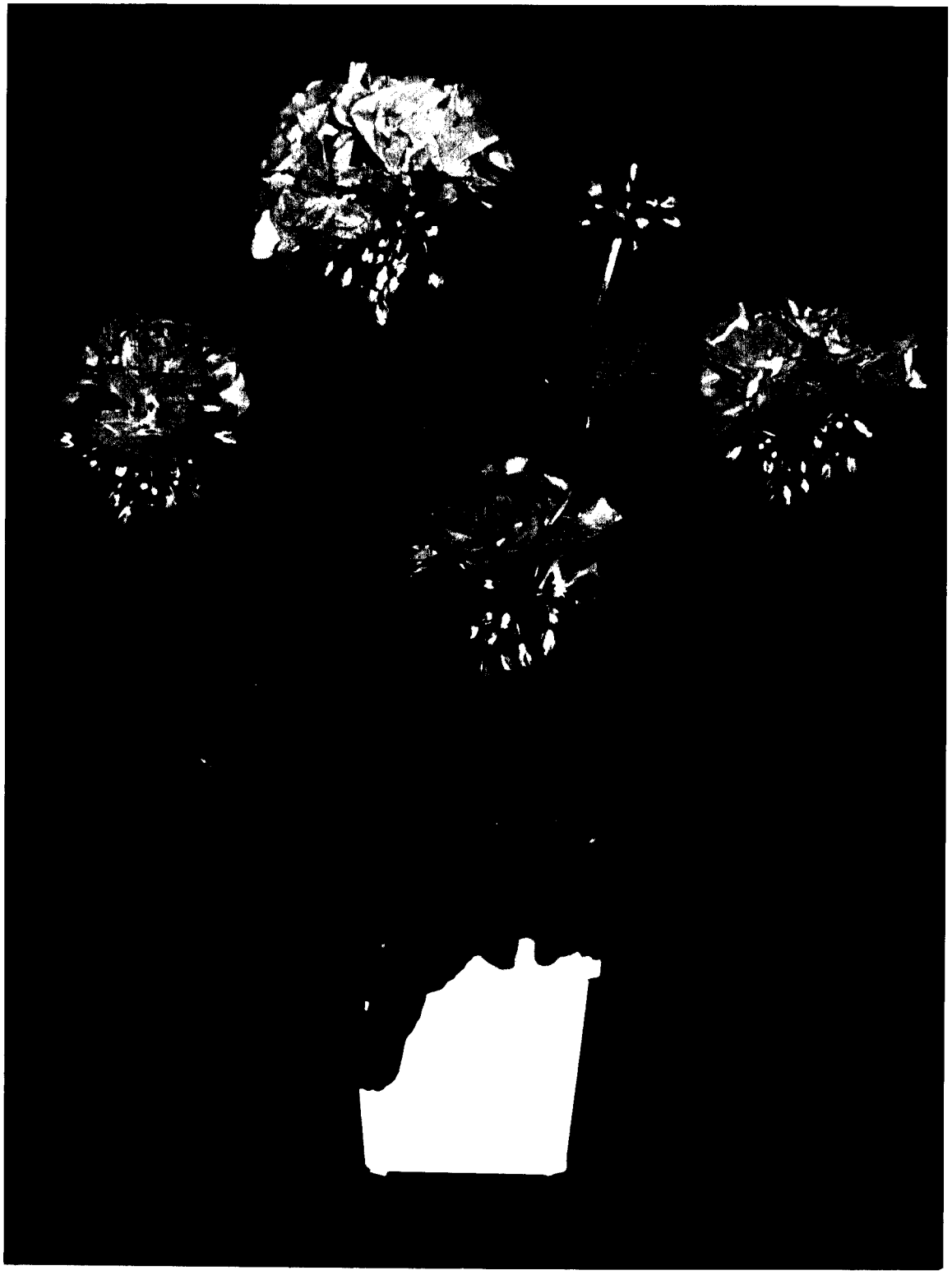

UNITED STATES PATENT AND TRADEMARK OFFICE

CERTIFICATE OF CORRECTION

PATENT NO. : Plant 7,576

DATED : July 2, 1991

INVENTOR(S) : Richard Craig

It is certified that error appears in the above-identified patent and that said Letters Patent is hereby corrected as shown below:

Column 1, lines 19-33: "

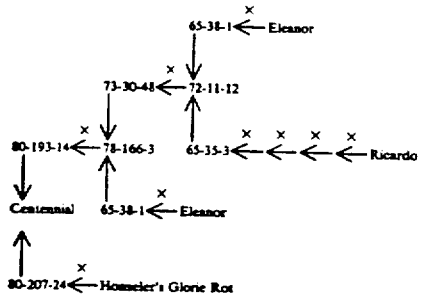

should read as:

--

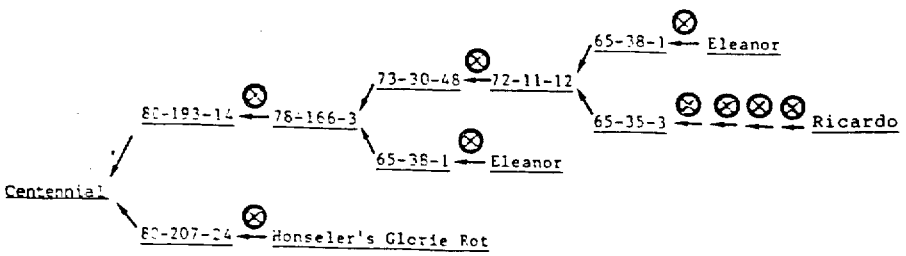

--

Signed and Sealed this

Tenth Day of November, 1992

*Attest:*

DOUGLAS B. COMER

*Attesting Officer*

*Acting Commissioner of Patents and Trademarks*